(12) United States Patent
Uchida et al.

(10) Patent No.: US 8,382,702 B2
(45) Date of Patent: Feb. 26, 2013

(54) FLUID INJECTION DEVICE AND MEDICAL INSTRUMENT INCLUDING FLUID INJECTION DEVICE

(75) Inventors: Kazuaki Uchida, Matsumoto (JP); Hideki Kojima, Matsumoto (JP); Atsuya Hirabayashi, Chino (JP)

(73) Assignee: Seiko Epson Corporation, Tokyo (JP)

( * ) Notice: Subject to any disclaimer, the term of this patent is extended or adjusted under 35 U.S.C. 154(b) by 14 days.

(21) Appl. No.: 13/209,543

(22) Filed: Aug. 15, 2011

(65) Prior Publication Data

US 2012/0046605 A1 Feb. 23, 2012

(30) Foreign Application Priority Data

Aug. 20, 2010 (JP) .................................. 2010-184761

(51) Int. Cl.
*A61M 31/00* (2006.01)
*A61M 1/00* (2006.01)
*A61M 5/00* (2006.01)

(52) U.S. Cl. ............ 604/67; 604/65; 604/118; 604/151; 604/246

(58) Field of Classification Search .................... 604/65, 604/67, 118, 121, 151, 152, 246
See application file for complete search history.

(56) References Cited

U.S. PATENT DOCUMENTS

| 7,901,374 B2 | 3/2011 | Seto et al. |
| 2011/0208224 A1 | 8/2011 | Kojima |

FOREIGN PATENT DOCUMENTS

| JP | 2005-152127 | 6/2005 |
| JP | 2008-082202 | 4/2008 |
| JP | 2011-167440 A | 9/2011 |
| JP | 2012-040121 A | 3/2012 |

*Primary Examiner* — Victoria P Shumate
(74) *Attorney, Agent, or Firm* — Workman Nydegger (57) ABSTRACT

Fluid is pressurized and supplied to a fluid chamber with a fluid pressurizing and supplying unit. The pressurized fluid within the fluid chamber is ejected through an injection nozzle by reduction of the volume of the fluid chamber caused by applying a driving voltage to a volume varying unit. In applying the driving voltage to the volume varying unit, the effect imposed on fluid injection by pressure fluctuations of the fluid pressurized and supplied to the fluid chamber is compensated by changing the voltage waveform of the driving voltage. When the pressure of the supply flow amount is decreased to a pressure lower than a predetermined pressure, the time intervals of the driving waveform are corrected. The maneuverability of a fluid injection device does not deteriorate even when the pressure of the fluid pressurized and supplied to the fluid chamber fluctuates.

6 Claims, 11 Drawing Sheets

FIG. 11 ized fluid to the fluid chamber; a fluid pressurizing and sup-
FLUID INJECTION DEVICE AND MEDICAL INSTRUMENT INCLUDING FLUID INJECTION DEVICE This application claims the benefit of priority to Japanese Application No. 2010-184761 filed Aug. 20, 2010, which application is incorporated by reference in its entirety.

BACKGROUND

1. Technical Field

Embodiments of the present invention relate to a fluid injection device which ejects pressurized fluid, and to a medical instrument including the fluid injection device.

2. Related Art

Technology has been developed that pressurizes fluid such as water and physiological saltwater and ejects the fluid toward living tissues or the like through an injection nozzle for incision or excision of the living tissues or for other purpose (JP-A-2005-152127). This technology can incise the target tissues, such as internal organs, without damaging vascular structures such as blood vessels, and can thus reduce injuries to the surrounding tissues. Accordingly, this technology is expected to decrease the burden of surgery performed on a patient.

In addition, a technology which intermittently ejects a flow of fluid in pulses for incision of living tissues by using a small quantity of injection flow has been proposed (JP-A-2008-082202). According to this technology, fluid to be ejected is supplied to a small fluid chamber, and the small fluid chamber is then pressurized by a rapid reduction of the volume of the fluid chamber such that a pulse flow of the fluid can be ejected through the injection nozzle.

In order to eject fluid from the nozzle, the area from the fluid chamber to the tip of the injection nozzle needs to be filled with a sufficient amount of the fluid supplied to an injection unit. When bubbles are contained in the supplied fluid, these bubbles are broken when the volume of the fluid chamber is reduced. In this case, appropriate injection of the fluid through pressurization of the fluid within the fluid chamber cannot be achieved.

To overcome this problem, the technology of pulse flow injection uses a variable pump (such as a piston pump) rather than a centrifugal pump (such as vane pump), which easily generates bubbles. A volume variable pump (such as piston pump) secures a sufficient flow amount for supplying fluid to the fluid chamber without generating bubbles.

The pressure of the fluid supplied by the volume variable type pump, however, easily varies. Because of the variability in the pressure, the maneuverability of the fluid injection device easily deteriorates or is decreased. When the pressure of the supplied fluid lowers, the amount of fluid supplied falls short of the necessary injection amount of the fluid to be ejected. As a result, the injection amount decreases considerably, and the incision capability, or the reaction felt by the operator at the time of fluid injection varies extremely. Therefore, in the case of the technology for pulsed injection of a fluid, a special pump which is of the volume variable type and that is equipped to reduce pressure fluctuations as much as possible and that maintains maneuverability is needed.

SUMMARY

Embodiments of the invention advantageously provide a technology capable of solving at least a part of the aforementioned problems arising from the related art. Embodiments of the invention provide or relate to a technology which does not deteriorate or that maintains the maneuverability of a fluid injection device even when pressure fluctuations are present in the supplied fluid.

APPLICATION EXAMPLE 1

This application example of the invention is directed to a fluid injection device which includes: an injection nozzle through which fluid is ejected; a fluid chamber connected with the injection nozzle, wherein the fluid to be ejected is supplied to the fluid chamber; a fluid pressurizing and supplying unit which pressurizes the fluid and supplies the pressurized fluid to the fluid chamber; a volume varying unit which deforms in response to a driving voltage applied to the volume varying unit to vary a volume of the fluid chamber; a driving voltage applying unit which applies the driving voltage having a predetermined voltage waveform to the volume varying unit with fluid supplied to the fluid chamber; and a memory unit which stores pressure fluctuation data associated with fluid pressurized and supplied to the fluid chamber.

The fluid pressurizing and supplying unit is a unit which pressurizes and supplies fluid to the fluid chamber. Pressure fluctuations are generated during supply of the fluid. The driving voltage applying unit compensates the driving voltage applied to the volume varying unit by changing the voltage waveform based on the pressure fluctuation data stored in the memory unit. A time interval between the voltage waveform produced by the driving voltage applied a first time and the voltage waveform produced by the driving voltage applied a second when the pressure fluctuation data is lower than a predetermined pressure is longer than the time interval between the voltage waveform produced by the driving voltage applied the first time and the voltage waveform produced by the driving voltage applied the second time when the pressure fluctuation data is higher than the predetermined pressure.

According to this configuration, fluid is pressurized and supplied to the fluid chamber by the fluid pressurizing and supplying unit, and the pressurized fluid within the fluid chamber is ejected through the injection nozzle by reduction of the volume of the fluid chamber caused by applying the driving voltage to the volume varying unit. In applying the driving voltage to the volume varying unit, the driving voltage applying unit compensates for the effect imposed on fluid injection by pressure fluctuations of the fluid pressurized and supplied to the fluid chamber by changing the voltage waveform of the driving voltage.

When the pressure of the fluid pressurized and supplied to the fluid chamber varies, the force of the fluid ejected through the injection nozzle changes. Moreover, when the voltage waveform of the driving voltage applied to the volume varying unit varies, the force of the fluid ejected through the injection nozzle changes as well. Thus, when the voltage waveform of the driving voltage is changed in such a manner that the effect produced by the pressure fluctuations of the fluid pressurized and supplied to the fluid chamber can be cancelled, the maneuverability of the fluid injection device does not deteriorate even when the pressure of the fluid pressurized and supplied to the fluid chamber varies.

The time interval between the voltage waveform produced by the driving voltage applied a first time and the voltage waveform produced by the driving voltage applied a second time when the supply pressure is lower than the predetermined pressure is longer than the time interval between the voltage waveform produced by the driving voltage applied the first time and the voltage waveform produced by the driving voltage applied the second time when the supply pressure is higher than the predetermined pressure.

In this case, when the supply pressure is lower than a predetermined pressure, the time interval between one injection and the subsequent injection can be prolonged. When the interval between injections (timing) is long or increased, a sufficient flow amount of the fluid can be securely supplied between one injection and the subsequent injection even under the pressure drop of the fluid pressurized and supplied from the supply pump. Thus, fluid can be supplied or ejected from the tip of the injection nozzle in an appropriate condition.

APPLICATION EXAMPLE 2

In the fluid injection device of the above application example, the driving voltage applying unit may be a unit which applies the driving voltage to the volume varying unit after changing the voltage waveform such that a maximum potential difference of the driving voltage increases as the pressure of the fluid pressurized and supplied to the fluid chamber decreases.

According to this configuration, the pressure of the fluid within the fluid chamber can be raised by changing the voltage waveform such that the maximum potential difference of the driving voltage increases. In this case, compensation for the pressure drop of the fluid pressurized and supplied into the fluid chamber can be achieved. Thus, even when the pressure of the fluid pressurized and supplied to the fluid chamber drops, the maneuverability of the fluid injection device does not deteriorate.

When the pressure of the fluid pressurized and supplied to the fluid chamber increases, the voltage waveform is changed such that the maximum potential difference of the driving voltage decreases as the pressure rises is applied to the volume varying unit. In this case, the pressure increase within the fluid chamber produced by changes in the volume of the fluid chamber is reduced, whereby compensation for the pressure increase of the fluid pressurized and supplied into the fluid chamber can be achieved. Thus, even when the pressure of the fluid pressurized and supplied to the fluid chamber rises, the maneuverability of the fluid injection device does not deteriorate.

APPLICATION EXAMPLE 3

In the fluid injection device of the above application example, the driving voltage applying unit may be a unit which applies the driving voltage to the volume varying unit after changing the voltage waveform such that the voltage increase rate of the driving voltage increases as the pressure of the fluid pressurized and supplied to the fluid chamber decreases.

According to this configuration, the pressure of the fluid within the fluid chamber can be raised by changing the voltage waveform such that the voltage increase rate of the driving voltage increases. In this case, compensation for the pressure drop of the fluid pressurized and supplied into the fluid chamber can be achieved. Thus, even when the pressure of the fluid pressurized and supplied into the fluid chamber lowers, the maneuverability of the fluid injection device does not deteriorate.

When the pressure of the fluid pressurized and supplied to the fluid chamber increases, the voltage waveform applied to the volume varying unit is changed such that the voltage increase rate of the driving voltage decreases as the pressure rises. In this case, the pressure increase within the fluid chamber produced by changes in the volume of the fluid chamber is reduced, whereby compensation for the pressure increase of the fluid pressurized and supplied into the fluid chamber can be achieved. Thus, even when the pressure of the fluid pressurized and supplied to the fluid chamber rises, the maneuverability of the fluid injection device does not deteriorate.

APPLICATION EXAMPLE 4

This application example of the invention is directed to a medical instrument which includes the fluid injection device of any of the above application examples.

According to this configuration, the fluid injection device of any of the above application examples is included. Thus, even when the pressure of the fluid pressurized and supplied into the fluid chamber fluctuates, the maneuverability of the fluid injection device does not deteriorate. Accordingly, the medical instrument can be operated in a stable condition.

An example of the medical instrument provided according to this application example of the invention is a water jet scalpel used for living body surgery. The medical instrument of this application example secures high-level safety and allows a doctor using the instrument to concentrate only on his or her medical treatment under a stable condition of maneuver or of maneuvering the medical instrument. Embodiments of the invention compensate for fluctuations in the pressure of the fluid supplied to the medical device such that the maneuverability of the medical device is maintained and does not deteriorate.

BRIEF DESCRIPTION OF THE DRAWINGS

Embodiments of the invention will be described with reference to the accompanying drawings, where like numbers reference like elements.

DESCRIPTION OF EXEMPLARY EMBODIMENT

Embodiments of the invention are hereinafter described in the following order for clarifying the details of embodiments the invention.

1. Device Structure
2. Fluid Injection Operation
3. Actuator Driving Method
4. Modification of Embodiment

1. Device Structure

Figure 1:
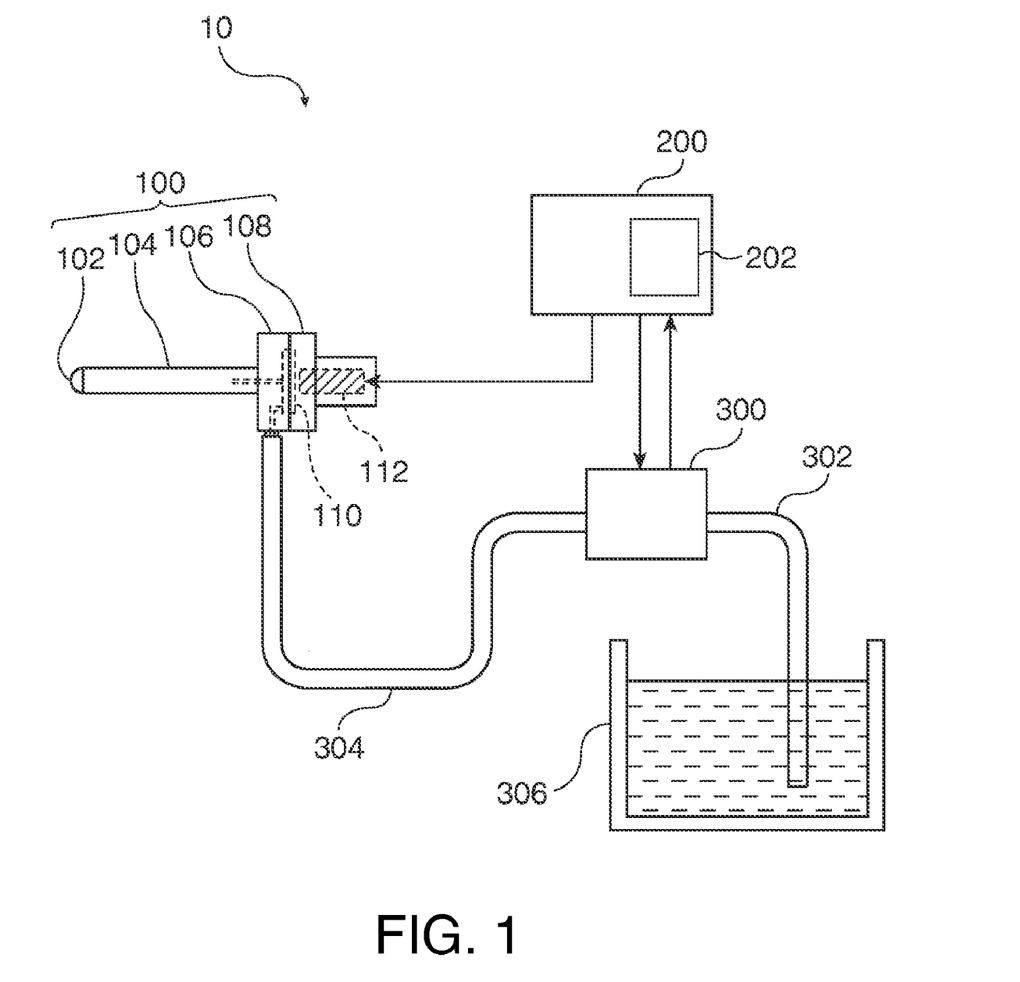
FIG. 1 illustrates a general structure of a fluid injection device according to an embodiment.

FIG. 1 schematically illustrates a general structure of a fluid injection device 10 according to this embodiment. As illustrated in FIG. 1, the fluid injection device 10 includes an injection unit 100 which ejects fluid in pulses, a supply pump 300 as a fluid pressurizing and supplying unit which pressurizes fluid and supplies the fluid to the injection unit 100 as fluid to be ejected from the injection unit 100, a control unit 200 which controls the operations of the injection unit 100 and the supply pump 300, and a memory section 202 as a memory unit which stores the pressure fluctuations of the supply from the supply pump 300 in advance. The memory section 202 may be contained in the control unit 200.

The injection unit 100 may have a substantially rectangular front block 106 made of metal, and a rear block 108 also made of metal. The rear block 108 may be overlapped with and fixed to the front block 106 by screws. A round-tube-shaped fluid channel tube 104 projects from a front surface of the front block 106. An injection nozzle 102 is configured as a nozzle for injection of the fluid. the injection nozzle 102 is inserted into a distal end of the fluid channel tube 104. A fluid chamber 110, configured as a thin disk-shaped fluid chamber, is provided at a junction between the front block 106 and the rear block 108 or on the surface of the junction. The fluid chamber 110 is connected with the injection nozzle 102 via the fluid channel tube 104. An actuator 112 is configured as a volume varying unit and is constituted by a laminated piezoelectric device. The actuator 112 is provided within the rear block 108 and is configured to change the volume of the fluid chamber 110. Deformation of the actuator 112 in response to driving voltage applied thereto causes in deformation of the fluid chamber 110.

The supply pump 300 sucks fluid to be ejected (such as water, physiological saltwater, and/or fluid medicine) from a fluid container 306 storing the fluid via a tube 302, and supplies the sucked fluid into the fluid chamber 110 of the injection unit 100 via a tube 304. It is required that the supply pump 300 supplies a sufficient amount of fluid to meet the requirement of the injection unit 100 while preventing bubbles from being mixed into the fluid. Thus, the supply pump 300 is constituted not by a centrifugal pump which pressurizes and supplies fluid by rotating a turbine-shaped component (called a vane or and impeller) within a case but by a volume variable pump (such as a piston pump or a diaphragm pump). The volume variable pump sucks fluid into a fluid chamber whose volume is variable and then decreases the volume of the fluid chamber to supply pressurized fluid. The details of this type of pump are not shown in FIG. 1.

According to this embodiment, the supply pump 300 included in the fluid injection device 10 is a piston pump which pressurizes and supplies fluid stored in the fluid chamber 110 by slidingly moving two pistons within a cylinder. The two pistons slidingly shift with respect to each other in opposite phases such that one piston advances during retreat of the other piston. According to this structure, pressurized fluid can be continuously supplied toward the injection unit 100 without a break. However, in the mechanism where only the two pistons move slidingly in opposite phases, the pressure at which the fluid is supplied cannot be equalized. Thus, the fluid supplied to the injection unit 100 involves or includes pressure fluctuations.

The control unit 200 regulates the operation of the fluid injection device 10 by controlling the actuator 112 included in the injection unit 100 and the supply pump 300. As noted above, the fluid injection device 10 supplies fluid containing or having pressure fluctuations from the supply pump 300 to the injection unit 100. The pressure fluctuation data of pressure fluctuations within the fluid chamber 110 associated with the fluid pressurized and supplied from the supply pump 300 is stored in the memory section 202 in advance of ejecting the fluid. The fluid injection device 10 changes the driving condition of the actuator 112 included in the injection unit 100 based on the pressure fluctuation data stored in the memory section 202. Thus, even when the fluid supplied to the injection unit 100 has pressure fluctuations, the maneuverability of the fluid injection device 10 does not deteriorate. The details of this point will be described later.

Figure 2A:
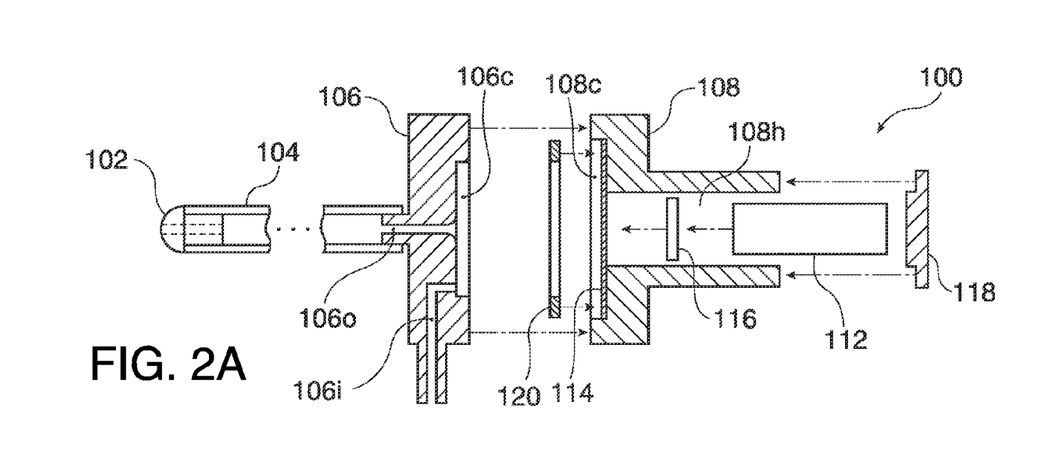
FIGS. 2A and 2B illustrate a detailed structure of an embodiment of an injection unit.
Figure 2B:
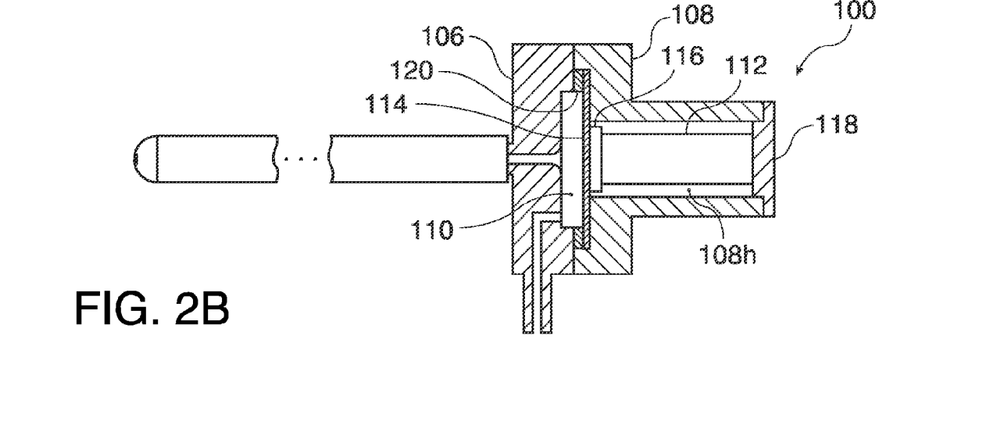

FIGS. 2A and 2B illustrate a detailed structure of the injection unit 100. FIG. 2A is a cross-sectional view of the injection unit 100 in a disassembled condition. FIG. 2B is a cross-sectional view of the injection unit 100 after assembly. A large, shallow and circular concave portion 108c is provided substantially at the center of the rear block 108 on the surface joined with the front block 106. A through hole 108h having a circular cross section is formed at the center of the concave portion 108c in such a manner so as to penetrate through the rear block 108.

A thin metal diaphragm 114 is provided on the bottom of the concave portion 108c in such a condition as to close the through hole 108h. The circumference of the diaphragm 114 is air-tightly secured to the bottom of the concave portion 108c by brazing, diffused junction or other methods. An annular metal reinforcing plate 120 is loosely fitted to the diaphragm 114 from the side opposite to the side of the diaphragm 114 facing towards the bottom of the concave portion 108c (from above as viewed in the figure). The thickness of the reinforcing plate 120 is determined or selected such that the position of the end surface of the rear block 108 on which the concave portion 108c is formed can be aligned with the position of the end surface of the reinforcing plate 120 when the reinforcing plate 120 is fitted to the concave portion 108c with the diaphragm 114 interposed therebetween.

The actuator 112 (laminated piezoelectric device in this embodiment) is inserted into the through hole 108h whose one end is closed by the diaphragm 114. The other end of the through hole 108h facing to the opposite side of the actuator 112 is closed by a disk-shaped metal bottom plate 118. A circular metal shim 116 is accommodated between the actuator 112 and the diaphragm 114. The thickness of the shim 116 is determined or selected such that the diaphragm 114, the shim 116, the actuator 112, and the bottom plate 118 contact each other when the through hole 108h of the rear block 108 accommodating the actuator 112 is closed by the bottom plate 118.

A circular and shallow concave portion 106c is formed on the surface of the front block 106 on the side joined with the rear block 108. The inside diameter of the concave portion 106c is set substantially at the same length as the inside diameter of the annular shape of the reinforcing plate 120 fitted to the rear block 108. The fluid chamber 110, being substantially disk shaped, is produced by the inner circumferential surfaces of the diaphragm 114 and the reinforcing plate 120 provided on the rear block 108 and by the concave portion 106c provided on the front block 106 when the front block 106 and the rear block 108 are joined and fixed to each other by screws.

The front block 106 has a supply channel 106i through which fluid is supplied from the side of the front block 106 to the fluid chamber 110. An injection channel 106o having a small diameter penetrates the center of the concave portion 106c as a channel through which the fluid pressurized at the fluid chamber 110 passes.

The fluid channel tube 104 is attached to the area of the front block 106 to which the injection channel 106o is opened by engagement between the inner surface of the fluid channel tube 104 defining the inside diameter thereof and the front block 106. The injection nozzle 102 is attached to the distal end of the fluid channel tube 104. In this arrangement, the channel for the fluid ejected from the injection unit 100 extends from the fluid chamber 110 toward the injection channel 106o where the cross-sectional area is reduced in the injection channel 106o, expands its cross-sectional area at the fluid channel tube 104, and again reduces its cross-sectional area at the injection nozzle 102 provided at the distal end of the fluid channel tube 104.

FIG. 2B is a cross-sectional view of the injection unit 100 in the assembled condition. As illustrated in FIG. 2B, the end surface of the reinforcing plate 120 is aligned with the end surface of the rear block 108, and the fluid chamber 110 is produced between the front block 106 and the rear block 108 when the front block 106 is aligned with these surfaces. In this arrangement, the diaphragm 114, the shim 116, the actuator 112, and the bottom plate 118 are brought into contact with each other when the bottom plate 118 is attached to the through hole 108h of the rear block 106 accommodating the shim 116 and the actuator 112.

2. Fluid Injection Operation

Figure 3A:
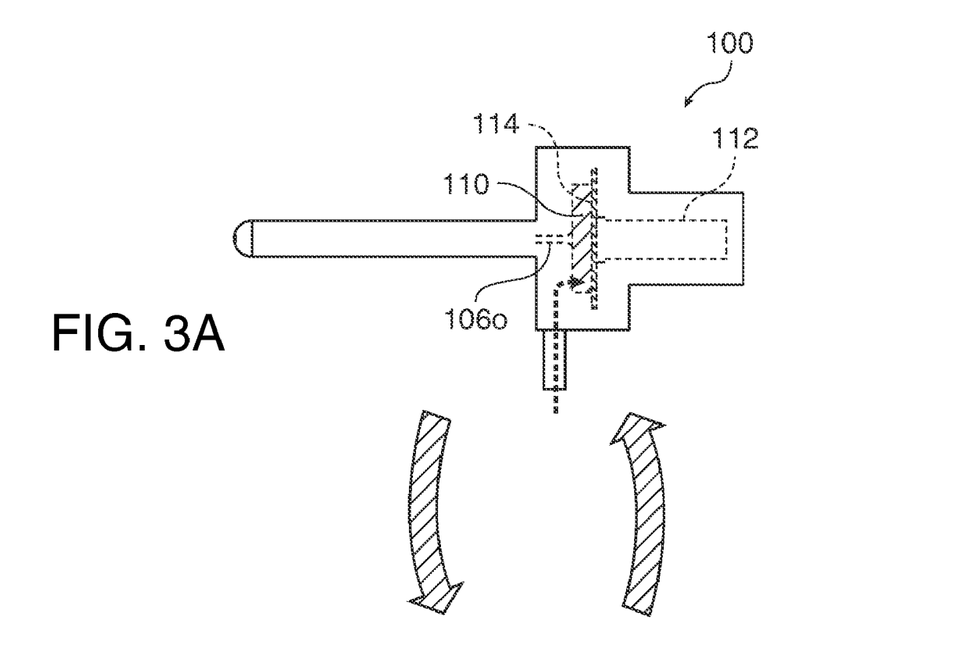
FIGS. 3A and 3B illustrate an operation of the injection unit for injection of fluid according to the embodiment.
Figure 3B:
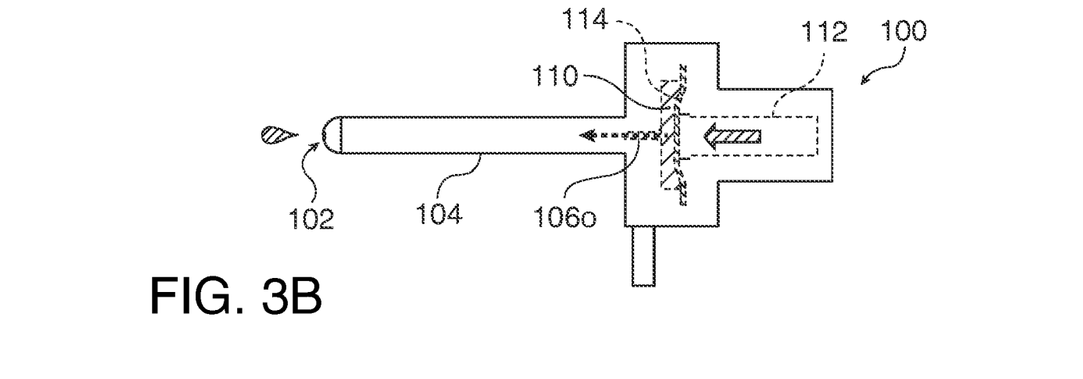

FIGS. 3A and 3B illustrate the operation of the injection unit 100 for ejecting fluid according to this embodiment. FIG. 3A shows the condition in which the actuator 112 is not operating (condition before a driving voltage is applied) during operation of the supply pump 300. Under this condition, the fluid chamber 110 is filled with fluid supplied by the supply pump 300 as indicated by a bold broken line in FIG. 3A. The fluid chamber 110 filled with fluid is represented by the crosshatched area in the figure.

Then, the driving voltage is applied to the actuator 112 to initiate operation of the actuator 112. As a result, the actuator 112 deforms in an extending direction to reduce the volume of the fluid chamber 110 by deformation of the diaphragm 114. By this process, the fluid in the fluid chamber 110 is pressurized and shifted toward the injection channel 106o and the fluid channel tube 104 to be ejected through the injection nozzle 102.

The fluid chamber 110 connects not only with the injection channel 106o but also with the supply channel 106i. According to this arrangement, it is considered that the fluid pressurized at the fluid chamber 110 flows out not only through the injection channel 106o but also through the supply channel 106i. In practice, however, the fluid pressurized at the fluid chamber 110 flows only through the injection channel 106o and does not pass through the supply channel 106i for the following reasons.

In this condition, the fluid within the supply channel 106i flows in such a direction as to come into the fluid chamber 110. Thus, for allowing the fluid pressurized at the fluid chamber 110 to flow out through the supply channel 106i, a force for pushing back the flow of the fluid within the supply channel 106i is required. Moreover, the force of the fluid within the supply channel 106i needs to surpass the pressure of fluid supply given by the supply pump 300.

On the other hand, there is no flow of fluid which prevents the fluid within the fluid chamber 110 from flowing out through the injection channel 106o. In addition, the pressure of fluid supplied by the supply pump 300 is not applied to the injection channel 106o in such a direction as to prevent the fluid from flowing out of the fluid chamber 110.

Therefore, the fluid pressurized at the fluid chamber 110 flows out through the injection channel 106o and not through the supply channel 106i. Furthermore, the inertance of the supply channel 106i can be raised to be higher than that of the injection channel 106o by controlling the cross-sectional areas and the lengths of the injection channel 106o and the supply channel 106i such that the fluid pressurized at the fluid chamber 110 can be directed to flow out through the injection channel 106o more easily by the higher inertance of the supply channel 106i.

For example, the inertance of the supply channel 106i can be made higher than that of the injection channel 106o by setting the cross-sectional area at the exit of the injection channel 106o (i.e., the cross-sectional area of the fluid channel tube 104) at a size larger than the cross-sectional area of the supply channel 106i, or by setting a length of the injection channel 106o at a length smaller than the length of the supply channel 106i.

For these reasons, the fluid pressurized at the fluid chamber 110 flows out only through the injection channel 106o and not through the supply channel 106i.

FIG. 3B shows a condition in which a driving voltage is applied to the actuator 112. In this condition in response to the driving voltage, the actuator 112 deforms to reduce the volume of the fluid chamber 110. As a result, the fluid pushed by the deformation of the diaphragm 114 is ejected in pulses through the injection nozzle 102.

After injection of the pulsed fluid, the voltage applied to the actuator 112 is removed. Consequently, the deformed actuator 112 returns to a shape having the original length, whereby the decreased volume of the fluid chamber 110 returns to the original volume. Simultaneously with these actions, fluid is supplied from the supply pump 300 to the fluid chamber 110. The result is a return to the condition prior to operation of the actuator 112 as shown in FIG. 3A. When the driving voltage is again applied to the actuator 112 under this condition, the fluid pushed out of the fluid chamber 110 in accordance with the deformation of the actuator 112 shown in FIG. 3B is ejected in pulses through the injection nozzle 102. According to the fluid injection device 10 in this embodiment, therefore, pulsed fluid can be ejected from the injection nozzle 102 every time the driving voltage is applied to the actuator 112.

Figure 4:
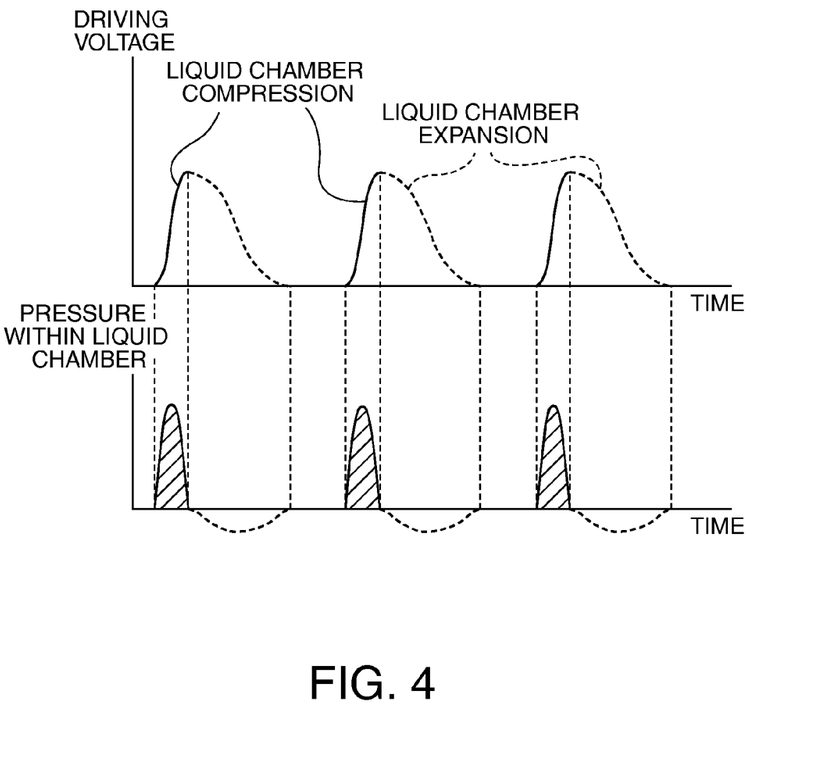
FIG. 4 conceptually illustrates a condition in which fluid within a fluid chamber is pressurized in response to a driving voltage applied to an actuator.

FIG. 4 conceptually illustrates a condition in which the fluid within the fluid chamber 110 is pressurized when the driving voltage is applied to the actuator 112. FIG. 4 shows only the raised or reduced pressure applied by the actuator 112, and does not include the pressure at which fluid is supplied from the supply pump 300 to the fluid chamber 110. The upper half of FIG. 4 corresponds to the driving voltage waveform applied to the actuator 112, while the lower half of FIG. 4 shows the change in the pressure within the fluid chamber 110 in response to the deformation of the fluid chamber 110 caused by the actuator 112.

According to this embodiment, the actuator 112, which deforms in an extending direction or which extends within the through hole 108h, decreases the volume of the fluid chamber 110 when the voltage applied to the actuator 112 rises, and increases the volume of the fluid chamber 110 when the applied voltage lowers. In other words, the volume of the fluid chamber 110 returns to the volume it had before the voltage applied to the actuator 112 rose.

The driving voltage waveform indicated by solid lines corresponds to compression of the fluid chamber 110, while the driving voltage waveform indicated by broken lines corresponds to expansion of the fluid chamber 110. In the range of compression of the fluid chamber 110 (range of driving voltage waveform indicated by solid lines), the fluid within the fluid chamber 110 is pressurized and the fluid is ejected from the injection nozzle 102. Then, in the range where the volume of the fluid chamber 110 returns to the original volume (range of driving voltage waveform indicated by broken lines), the pressure of the fluid chamber 110 lowers and fluid is supplied through the supply channel 106i into the fluid chamber 110. When the pressure of the fluid supplied from the supply pump 300 fluctuates, the following phenomenon occurs.

Figure 5A:
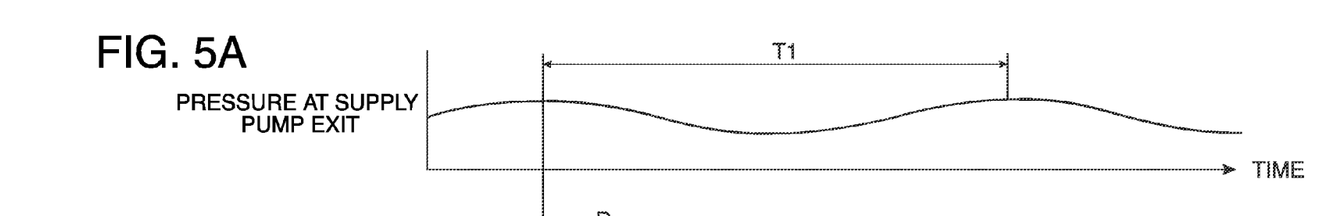
FIGS. 5A through 5C conceptually illustrate a phenomenon produced when fluid containing pressure fluctuations is supplied from a supply pump.

FIGS. 5A through 5C conceptually shows phenomenon caused when the fluid supplied by the supply pump 300 toward the injection unit 100 contains or includes pressure fluctuations. For example, the fluid pressure at the exit of the supply pump 300 varies in a cycle T1 as illustrated in FIG. 5A. This pressure fluctuation produces a slight delay D at the tube 304 connecting the supply pump 300 and the injection unit 100 (entrance of fluid chamber 110), and slightly decreases the pressure amplitude.

Figure 5B:
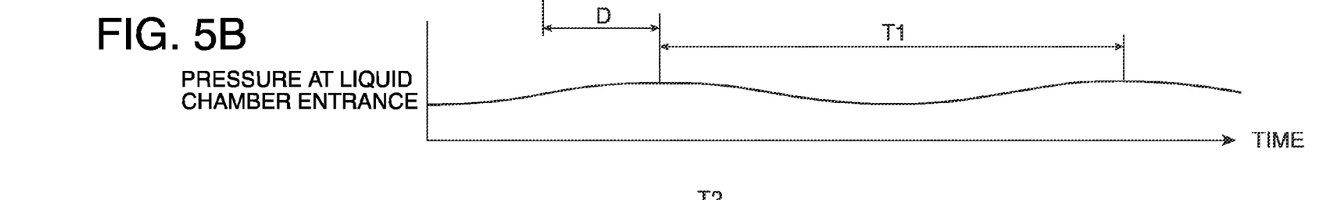

As a result, fluid containing the pressure fluctuations shown in FIG. 5B is supplied to the fluid chamber 110 of the injection unit 100. Thus, while the actuator 112 is not operating, the pressure within the fluid chamber 110 varies according to the condition shown in FIG. 5B. The memory section 202 stores the pressure fluctuation data of the pressure fluctuations within the fluid chamber 110 shown in FIG. 5B.

Under the pressure within the fluid chamber 110 shown in FIG. 5B, the actuator 112 is driven by the driving voltage having the waveform shown in FIG. 4. In this case, the pressure within the fluid chamber 110 increases or decreases in accordance with compression or expansion of the fluid chamber 110 caused by the actuator 112. As a result, the pressure within the fluid chamber 110 varies in such a condition that the short-cycle fluctuation varying according to a cycle T2 is superposed on the long-cycle fluctuation varying according to the cycle T1 as shown in FIG. 5C when the driving voltage waveform having the cycle T2 described later is applied to the actuator 112, for example.

Figure 5C:
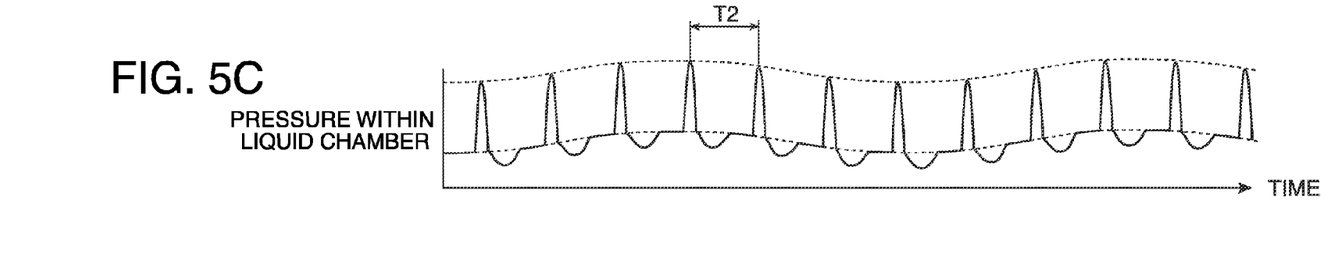

When the pressure within the fluid chamber 110 fluctuates according to the condition shown in FIG. 5C, the maneuverability of the fluid injection device 10 deteriorates for the following reasons.

The fluid is ejected from the injection nozzle 102 in pulses at the intervals of the cycle T2. In this case, the force of injection of the fluid varies for each pulse. Thus, the level of incision for living tissues changes and causes excessive cutting or insufficient cutting of the tissues. Since the pressure outside the injection nozzles 102 is kept at the atmospheric pressure, the flow amount of the fluid ejected from the injection nozzle 102 varies in accordance with the fluctuations of the pressure within the fluid chamber 110. As a consequence, the level of incision for living tissues also changes in accordance with the variations in the flow amount of the ejected fluid.

When the fluid is ejected from the injection nozzle 102, the reaction force is transmitted to the injection unit 100. Thus, when the force of the fluid ejected from the injection nozzle 102 varies, the force necessary for holding the injection unit 100 changes. In this case, holding the injection unit 100 at the same position is difficult for the operator of the fluid injection device 10.

Furthermore, when the fluid is ejected from the injection nozzle 102, the injection nozzle 102 and a part of the interior of the fluid channel tube 104 connecting the injection nozzle 102 and the fluid chamber 110 become an area that is not filled with fluid immediately after the injection of the fluid. Thus, the space from these portions to the tip of the injection nozzle 102 need to be filled with fluid pressurized and supplied from the supply pump 300 during the period before the next injection of fluid. Generally, the flow amount of pressurized and supplied fluid decreases as the pressure of the pressurized and supplied fluid lowers. Thus, when the pressure of the fluid pressurized and supplied from the supply pump 300 is lower than a predetermined pressure, there is a possibility that the space up to the tip of the injection nozzle 102 cannot be filled with fluid by the next injection due to the insufficient amount of the fluid pressurized and supplied from the supply pump 300 after one injection of fluid under a pressure lower than the predetermined pressure.

When the space up to the tip of the injection nozzle 102 is not filled with fluid, the flow amount of fluid to be ejected from the injection nozzle 102 decreases. As a result, the problem of insufficient incision for living tissues occurs. Since the force of the fluid ejected from the injection nozzle 102 varies, the force necessary for supporting the injection unit 100 changes. In this case, holding the injection unit 100 at the same position is difficult for the operator of the fluid injection device 10.

For these reasons, the maneuverability of the fluid injection device 10 deteriorates when the supply pressure of the supply pump 300 fluctuates. Therefore, the fluid injection device 10 in this embodiment changes the voltage waveform applied to the actuator 112 in accordance with the pressure at which the fluid is supplied from the supply pump 300. The fluid injection device also corrects the time interval between one injection and the subsequent injection when the supply pressure becomes lower than the predetermined pressure. By this method, deterioration of the maneuverability of the fluid injection device 10 can be prevented even when the fluid from the supply pump 300 contains pressure fluctuations.

3. Actuator Driving Method

Figure 6:
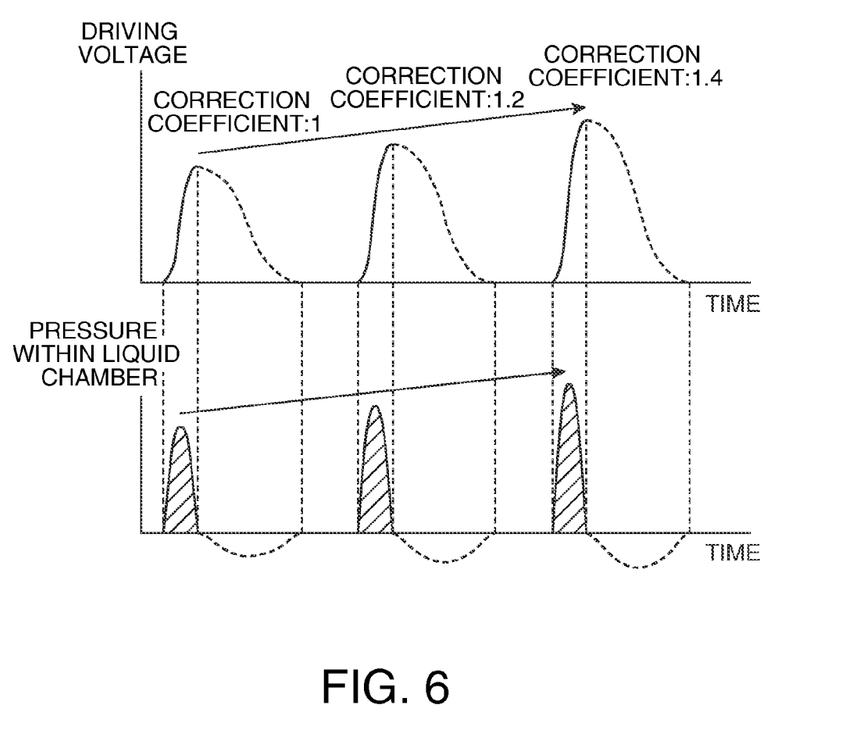
FIG. 6 illustrates a condition in which the fluid injection device changes the waveform of the driving voltage applied to the actuator according to the embodiment.

FIG. 6 shows the condition in which the fluid injection device 10 in this embodiment changes the driving voltage waveform applied to the actuator 112. This embodiment varies the driving voltage waveform applied to the actuator 112 by multiplying the driving voltage waveform stored as a reference waveform by correction coefficients. For example, the driving voltage waveform at the left end of the graph in the upper half of FIG. 6 is a waveform multiplied by the correction coefficient "1" (i.e., reference driving voltage waveform), the driving voltage waveform shown at the center is a waveform multiplied by the correction coefficient "1.2", and the driving voltage waveform shown at the right end is a waveform multiplied by the correction coefficient "1.4".

The lower half in FIG. 6 shows the condition in which the pressure within the fluid chamber 110 changes in accordance with the respective shapes of the driving voltage waveform shown in the upper half. As can be seen from FIG. 6, the peak pressure generated within the fluid chamber 110 increases as the correction coefficient becomes higher (as the maximum voltage of the driving voltage waveform becomes higher). On the other hand, the peak pressure generated within the fluid chamber 110 decreases as the correction coefficient becomes lower. According to the fluid injection device 10 in this embodiment, deterioration of the maneuverability of the fluid injection device 10 caused by pressure fluctuations of the fluid supplied from the supply pump 300 can be prevented by multiplying the driving voltage waveform applied to the actuator 112 by the correction coefficients.

Figure 7A:
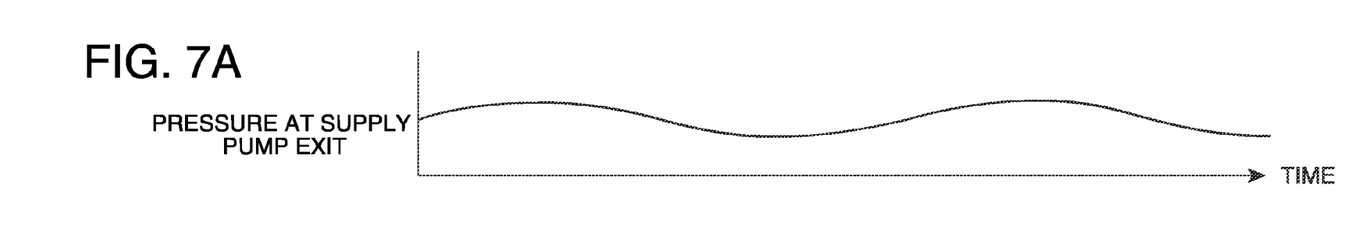
FIGS. 7A through 7C illustrate a condition in which the fluid injection device keeps the pressure peak constant by multiplying the driving voltage waveform using correction coefficients according to the embodiment.
Figure 7B:
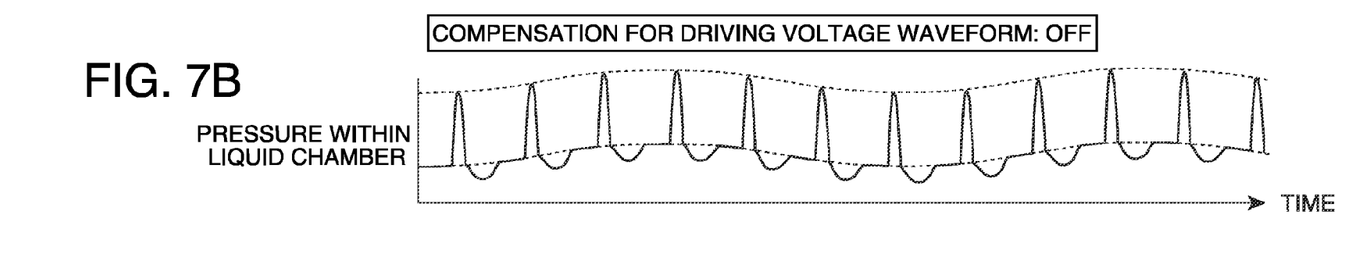
Figure 7C:
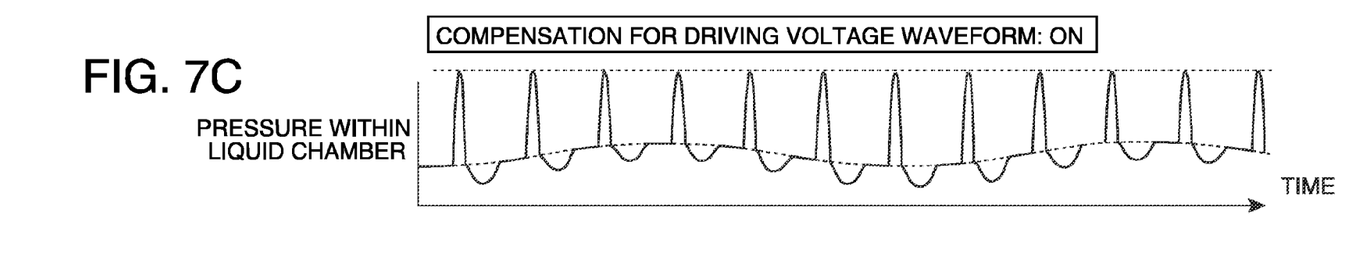

FIGS. 7A through 7C illustrate that the fluctuation of the fluid supply pressure from the supply pump 300 can be cancelled by multiplying the driving voltage waveform by the correction coefficients so that the peak pressure within the fluid chamber 110 can be kept constant according to the fluid injection device 10 in this embodiment. FIGS. 7A through 7C do not contain the effect of correction for the time interval between one injection and the subsequent injection when the supply pressure is lower than the predetermined pressure.

When the pressure at which fluid is pressurized and supplied from the supply pump 300 varies as illustrated in FIG. 7A, the pressure within the fluid chamber 110 fluctuates in the manner shown in FIG. 7B during operation of the actuator 112 under the reference driving voltage waveform (not multiplied by correction coefficients). In this case, the maneuverability of the fluid injection device 10 deteriorates as explained with reference to FIGS. 5A through 5C.

However, the peak pressure within the fluid chamber 110 in the range where the pressure of the fluid supplied to the fluid chamber 110 is low can be kept constant or substantially constant at the same level by applying the driving voltage waveform multiplied by correction coefficients larger than "1" to the actuator 112 as illustrated in FIG. 7C. When appropriate correction coefficients are determined in advance based on the pressure fluctuation data for pressure fluctuations within the fluid chamber 110 stored in the memory section 202, the peak pressure within the fluid chamber 110 can be kept substantially constant as shown in FIG. 7C.

The memory section 202 may be disposed within the supply pump 300. When the memory section 202 is located within the supply pump 300, the memory section 202 may store supply pressure fluctuation data for pressure fluctuations at the exit of the supply pump 300 as shown in FIG. 5A. While the pressure fluctuations of the fluid supplied to the fluid chamber 110 involve phase delay, amplitude attenuation and the like in the pressure fluctuations of the fluid pressurized and supplied by the supply pump 300, these factors are determined by the length of the tube 304 connecting the supply pump 300 and the injection unit 100, the rigidity of the tube 304 and other conditions to a large degree and thus can be predicted beforehand. Therefore, the correction coefficients of the driving voltage waveform may be calculated from the pressure fluctuations within the fluid chamber 110 that are based on the supply pressure fluctuation data for pressure fluctuations at the exit of the supply pump 300 as data stored in the memory section 202 provided within the supply pump 300.

For easy understanding of FIG. 5B, the delay D produced at the tube 304 is exaggerated as a great delay in the FIG. 5B. However, the actual delay D is not a long delay. Thus, for simplifying the calculation, the correction coefficients of the driving voltage waveform may be obtained without taking the effect of the delay D into account. In one embodiment, only the attenuation of the pressure fluctuations produced by the tube 304 are taken into consideration. While FIG. 7C shows the case in which the pulsed fluid is ejected inconstant cycles, the peak pressure can be made substantially constant for each pulse even in the case of fluid injection effected using arbitrary timing as well as fluid injection in constant cycles.

When the pressure of the fluid ejected from the injection nozzle 102 is kept substantially constant under the driving voltage waveform multiplied by the correction coefficients, the level of incision provided by the fluid injection device 10 can be maintained substantially constant. In addition, the flow amount of the fluid ejected in pulses can be maintained substantially constant for each injection. Furthermore, the reaction force applied to the injection unit 100 when the fluid is ejected from the injection nozzle 102 can be maintained substantially constant. Thus, even when the pressure of the fluid pressurized and supplied from the supply pump 300 fluctuates, the maneuverability of the fluid injection device 10 does not deteriorate.

Figure 8:
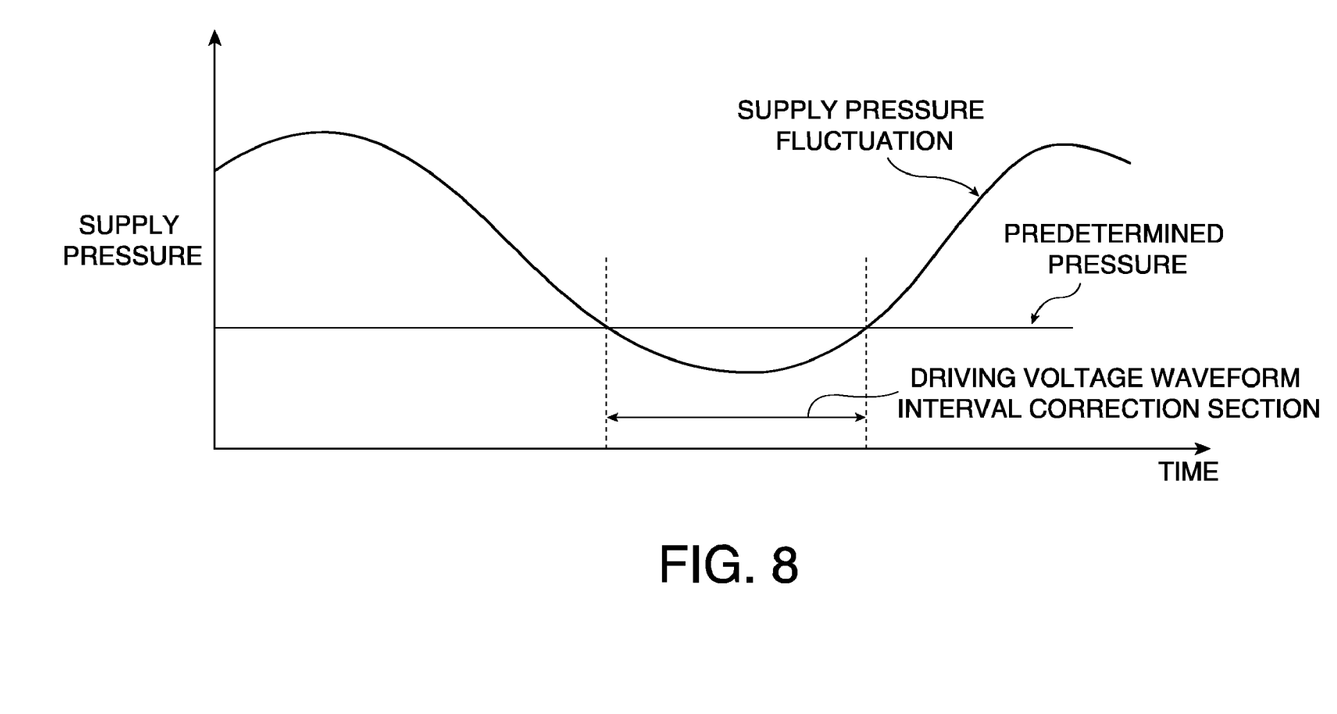
FIG. 8 illustrates a condition in which a predetermined pressure is determined when fluid containing pressure fluctuations is supplied from the supply pump.

Correction for the time interval between one injection and the subsequent injection when the supply pressure is lower than a predetermined pressure is now explained. FIG. 8 shows a predetermined pressure determined for the change of the time interval between one injection and the subsequent injection under the varying supply pressure. According to this correction, the time interval of the driving voltage waveform is changed when the supply pressure is lower than the predetermined pressure.

Figure 9:
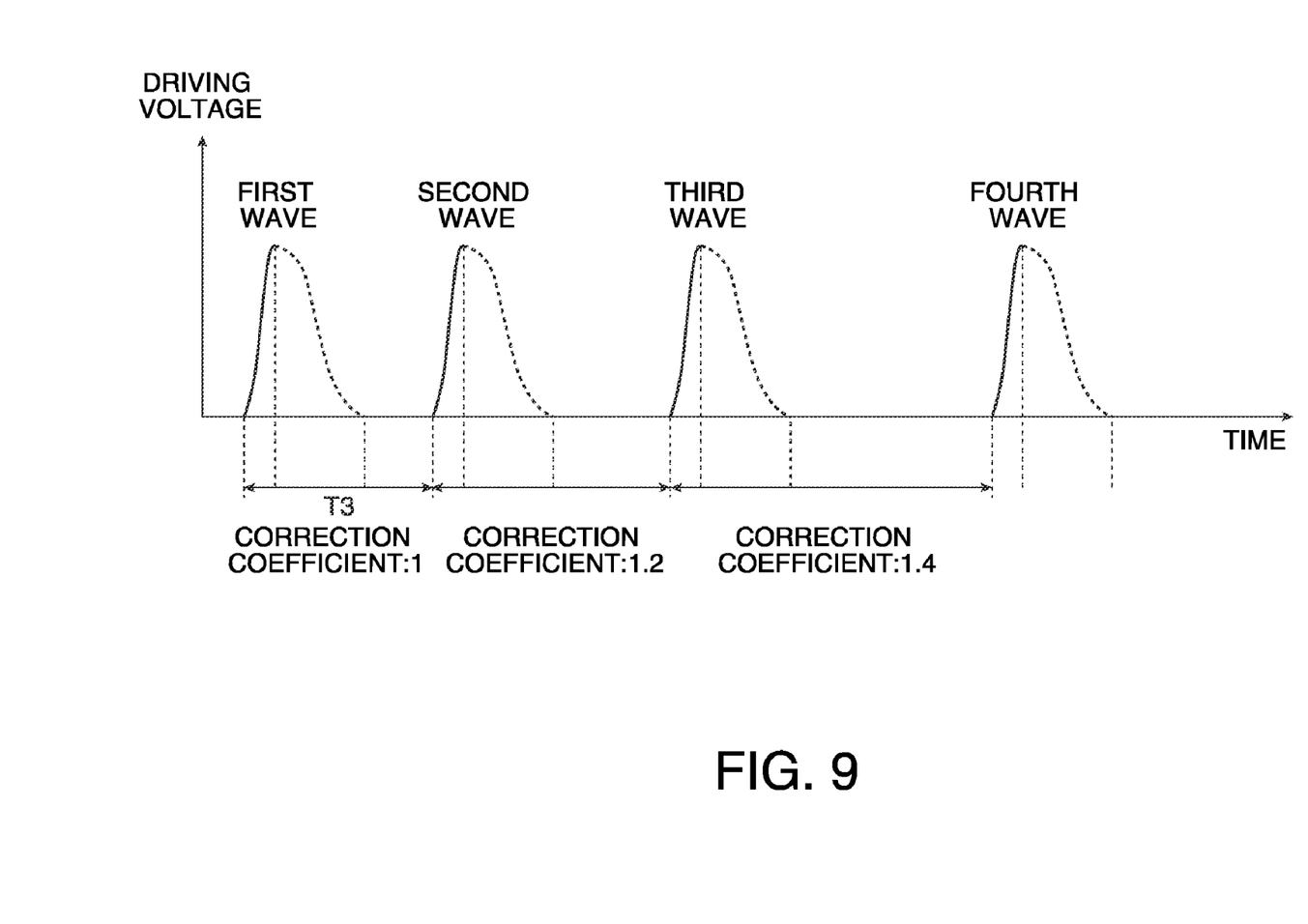
FIG. 9 illustrates a condition in which the fluid injection device changes the intervals of the driving voltage waveform applied to the actuator according to the embodiment.

FIG. 9 illustrates the condition in which the fluid injection device 10 in this embodiment changes the time intervals of the driving voltage waveform applied to the actuator 112. FIG. 9 shows only the waveform intervals and does not include the effect of the voltage correction explained above. It is assumed that the driving voltage waveform applied to the volume varying unit for injection of fluid of one pulse is constituted by a pair of the voltage increasing range (range of driving voltage waveform indicated by solid line) and the voltage decreasing range (range of driving voltage waveform indicated by broken line) similar to those shown in FIG. 4.

As illustrated in FIG. 9, the interval of injection of the pulsed fluid is represented by a time interval T3 between the start point of a voltage increasing range and the start point of the subsequent voltage increasing range. Thus, the driving voltage waveform is changed such that the time interval T3 increases in accordance with the supply voltage drop. For example, when waves of the driving voltage waveform at the first through fourth positions in the direction from the left to the right in the figure are a first wave, a second wave, a third wave, and a fourth wave, the time interval T3 of the driving voltage waveform between the first wave and the second wave is a waveform multiplied by the correction coefficient "1" (i.e., reference driving voltage waveform interval). Similarly, the driving voltage waveform interval between the second wave and the third wave is a waveform multiplied by the correction coefficient "1.2", and the driving voltage waveform interval between the third wave and the fourth wave is a waveform multiplied by the correction coefficient "1.4".

The period for supplying the fluid from the supply pump 300 into the fluid chamber 110 increases as the correction coefficient becomes larger (driving voltage waveform interval becomes longer). Thus, even when the supply flow amount is decreased due to the low supply pressure of the supply pump 300, the area up to the tip of the injection nozzle 102 can be filled with fluid by supply of fluid for a sufficient period. Accordingly, deterioration of the maneuverability of the fluid injection device 10 caused by the pressure fluctuations of the fluid from the supply pump 300 can be prevented by multiplying the interval of the driving voltage waveform applied to the actuator 112 by the correction coefficients.

The predetermined pressure may be established in the following manner. The relationship between the supply pressure and the supply flow amount can be determined by the length of the tube 304 connecting the supply pump 300 and the injection unit 100, the shapes of the channels within the injection unit 100 and/or the like, and thus can be predicted beforehand. In this case, the flow amount supplied to the injection unit 100 during the time interval T3 can be calculated from supply pressure fluctuation data stored in a memory section 400. The injection flow amount is not affected by the pressure fluctuations of the supply pump 300 but is kept substantially constant by the drive voltage correction explained above. Thus, the supply pressure at which the relation (flow amount supplied during reference time interval T3)=(flow amount of fluid ejected for one pulse) holds can be determined as the predetermined pressure.

It is preferable that the predetermined pressure lies in the range between the lower limit pressure and the upper limit pressure in the supply pressure fluctuations. When the predetermined pressure is set at a pressure equal to or lower than the lower limit pressure in the supply pressure fluctuations, the relation (flow amount supplied during reference time interval T3)≧(fluid ejected for one pulse) constantly holds. In this case, fluid flows from the injection nozzle 102 as well as the flow amount ejected as pulses. Thus, the additional amount of the fluid supplied thereby is wasted. On the other hand, when the predetermined pressure is set at a pressure equal to or higher than the upper limit pressure in the supply pressure fluctuations, the relation (flow amount supplied during reference time interval T3)≦(fluid ejected for one pulse) constantly holds. In this case, the supply flow amount is constantly insufficient, and the correction for the waveform interval is constantly required.

Figure 10:
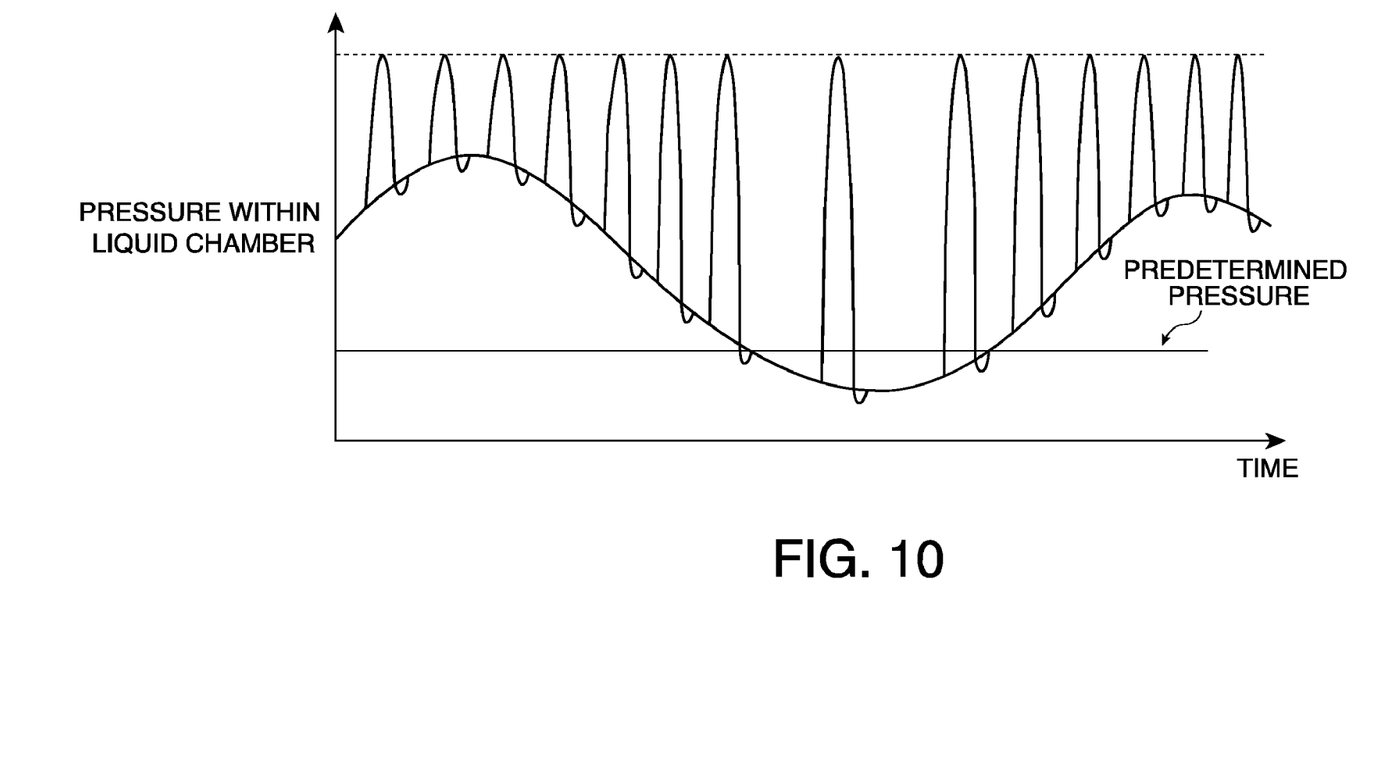
FIG. 10 illustrates a condition in which the fluid injection device controls the time intervals of injection while keeping the pressure peak constant within the fluid chamber by correcting the time intervals of the driving voltage waveform under a pressure lower than a predetermined pressure as well as by multiplying the driving voltage waveform using the correction coefficients according to the embodiment.

FIG. 10 illustrates control over the injection time interval while maintaining the constant peak pressure within the fluid chamber 110 by multiplying the time interval between the driving voltage waveform produced by applying the driving voltage once and the driving voltage waveform produced by applying the driving voltage next time by a correction coefficient for each time when the supply pressure is lower than the predetermined pressure, as well as by multiplying the driving voltage waveform by correction coefficients according to the fluid injection device 10 in this embodiment. In this control, the peak pressure within the fluid chamber 110 is kept substantially constant by multiplying the driving voltage waveform by the correction coefficients. Moreover, the area up to the tip of the injection nozzle 102 is kept filled with fluid even under the condition of supply pressure drop by multiplying the driving voltage waveform intervals by the correction coefficients when the supply pressure is lower than the predetermined pressure such that the fluid can be appropriately ejected from the tip of the injection nozzle 102. The waveform in this embodiment is only an example, and can be other waveforms such as rectangular waves and triangular waves.

4. Modification of Embodiment

According to this embodiment, the driving voltage waveform is deformed by multiplying the driving voltage waveform applied to the actuator 112 by the correction coefficients while maintaining a similar shape of the driving voltage waveform (i.e., expansion or reduction) such that the effect of the pressure fluctuations produced by the supply pump 300 can be compensated. However, the effect of the pressure fluctuations caused by the supply pump 300 may be corrected by deforming the driving voltage waveform into a non-similar shape. A modification of the embodiment including this change is hereinafter described.

Figure 11:
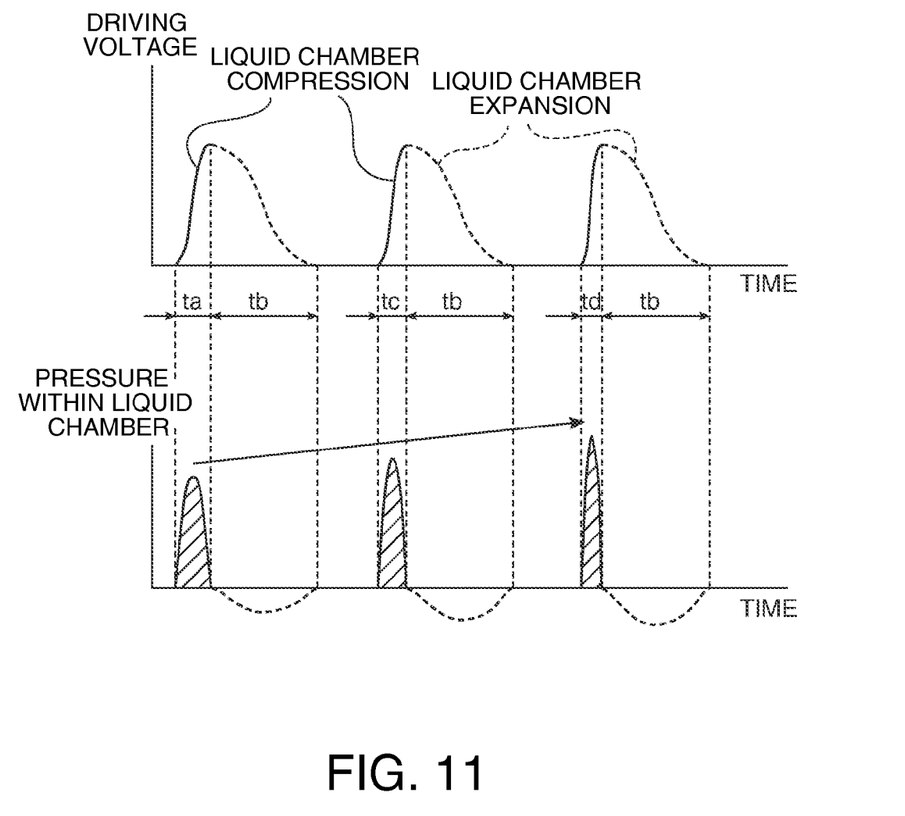
FIG. 11 illustrates a condition in which the fluid injection device according to a modified example of the embodiment changes the driving voltage waveform.

FIG. 11 illustrates a change of the driving voltage waveform produced by the fluid injection device 10 according to a modified example of the embodiment. The voltage waveform at the left end in three shapes shown in the upper half of FIG. 11 corresponds to the driving voltage waveform stored as a reference. The driving voltage waveform shown at the center is the voltage waveform produced by reducing the time necessary for output of the voltage increasing range from a reference time ta to a time tc (=0.8×ta). The driving voltage waveform shown at the right end corresponds to the voltage waveform produced by further reducing the time for output of the voltage increasing range to td (=0.6×ta).

According to this modified example of the embodiment, the driving voltage waveform applied to the actuator 112 is divided into the range which increases the driving voltage (voltage increasing range) and the range which decreases the driving voltage (voltage decreasing range), and the divided ranges are separately stored. Then, the driving voltage waveform applied to the actuator 112 is deformed by changing the time required for outputting the voltage increasing range. For example, in the case of the driving voltage waveform stored as the reference whose voltage increasing range takes the time ta to be outputted and whose voltage decreasing range takes the time tb to be outputted after the end of the voltage increasing range, this driving voltage waveform is deformed by shortening or prolonging the time required for outputting the voltage increasing range. It is also possible to change the time tb for the voltage decreasing range as well as the change of the time ta for the voltage increasing range.

When the time necessary for outputting the voltage increasing range is shortened, the voltage applied to the actuator 112 sharply rises. In this case, the actuator 112 rapidly deforms and sharply decreases the volume of the fluid chamber 110. As a result, the peak pressure applied to the fluid within the fluid chamber 110 increases.

The lower half in FIG. 11 shows the increase of the peak pressure within the fluid chamber 110 in accordance with the reduction of the time for the voltage increasing range of the driving voltage waveform. FIG. 11 shows only the case of reduction of the time required for outputting the voltage increasing range. When the time for outputting the voltage increasing range is prolonged, the peak pressure within the fluid chamber 110 decreases.

According to the fluid injection device 10 in the embodiment, the driving voltage waveform is deformed by multiplication by the correction coefficients determined based on the pressure fluctuation data stored in the memory section 202. In the case of the fluid injection device 10 in the modified example of the embodiment, the driving voltage waveform is deformed by shortening (or prolonging) the time required for outputting the voltage increasing range based on the pressure fluctuation data stored in the memory section 202. By this method, however, deterioration of the maneuverability caused by the effect of the pressure fluctuations of the fluid supplied from the supply pump 300 can be similarly avoided. When the pressure of the supplied fluid drops to a pressure equal to or lower than the predetermined pressure, the time interval between one injection and the subsequent injection is corrected in the manner described above along with the correction of the peak pressure within the fluid chamber 110 to a substantially constant pressure by multiplying the time ta for the voltage increasing range by the correction coefficients.

The waveform shown in this modified example is only an example and may be other waveforms such as triangular waves and saw-tooth waves.

While the fluid injection device 10 according to the embodiment has been discussed, the invention is not limited to the embodiment and modified example described herein but may be practiced otherwise without departing from the scope and spirit of the invention.

What is claimed is:

1. A fluid injection device comprising:
an injection nozzle through which fluid is ejected;
a fluid chamber connected with the injection nozzle, wherein the fluid to be ejected is supplied to the fluid chamber;
a fluid pressurizing and supplying unit which pressurizes the fluid and supplies the pressurized fluid to the fluid chamber;
a volume varying unit which deforms in response to a driving voltage applied to the volume varying unit to vary a volume of the fluid chamber;
a driving voltage applying unit which applies the driving voltage having a predetermined voltage waveform to the volume varying unit with fluid supplied to the fluid chamber; and
a memory unit which stores pressure fluctuation data associated with fluid pressurized and supplied to the fluid chamber,
wherein
the fluid pressurizing and supplying unit is a unit which pressurizes and supplies fluid to the fluid chamber with pressure fluctuations generated during supply of the pressurized fluid,
the driving voltage applying unit applies the driving voltage to the volume varying unit, wherein the driving voltage applying unit compensates the driving voltage by changing the voltage waveform based on the pressure fluctuation data stored in the memory unit, and
a time interval between the voltage waveform produced by the driving voltage applied a first time and the voltage waveform produced by the driving voltage applied a second time when the pressure fluctuation data is lower than a predetermined pressure is longer than the time interval between the voltage waveform produced by the driving voltage applied the first time and the voltage waveform produced by the driving voltage applied the second time when the pressure fluctuation data is higher than the predetermined pressure.

2. The fluid injection device according to claim 1, wherein the driving voltage applying unit is a unit which applies the driving voltage to the volume varying unit after changing the voltage waveform such that a maximum potential difference of the driving voltage increases as the pressure of the fluid pressurized and supplied to the fluid chamber decreases.

3. The fluid injection device according to claim 1, wherein the driving voltage applying unit is a unit which applies the driving voltage to the volume varying unit after changing the voltage waveform such that the voltage changing rate of the driving voltage increases as the pressure of the fluid pressurized and supplied to the fluid chamber decreases.

4. A fluid injection device comprising:
an injection nozzle through which fluid is ejected;
a fluid chamber connected with the injection nozzle, wherein the fluid to be ejected is supplied to the fluid chamber;
a fluid pressurizing and supplying unit which pressurizes the fluid and supplies the pressurized fluid to the fluid chamber;
a volume varying unit which deforms in response to a driving voltage applied to the volume varying unit to vary a volume of the fluid chamber;
a driving voltage applying unit which applies the driving voltage having a predetermined voltage waveform to the volume varying unit with fluid supplied to the fluid chamber;
a memory unit which stores pressure fluctuation data associated with fluid pressurized and supplied to the fluid chamber, and
a controller that compensates the driving voltage for pressure fluctuations in the pressurized fluid by applying correction coefficients to one or more of the waveforms of the driving voltage and adjusting an between waveforms of the driving voltage.

5. The fluid injection device of claim 4, wherein the controller compensates the driving voltage according to predetermined pressure fluctuation data stored in a memory.

6. The fluid injection device of claim 5, wherein the controller compensates the driving voltage to keep a peak pressure of within the fluid chamber substantially constant.

* * * * *